United States Patent [19]

Löbermann et al.

[11] Patent Number: 5,047,506

[45] Date of Patent: Sep. 10, 1991

[54] METHOD FOR THE PURIFICATION OF FACTOR XIII BY AFFINITY CHROMATOGRAPHY

[75] Inventors: Hartmut Löbermann, Schallstadt; Jürgen Römisch, Marburg; Werner Stüber, Lahntal, all of Fed. Rep. of Germany

[73] Assignee: Behringwerke Aktiengesellschaft, Marburg/Lahn, Fed. Rep. of Germany

[21] Appl. No.: 321,133

[22] Filed: Mar. 9, 1989

[30] Foreign Application Priority Data

Mar. 11, 1988 [DE] Fed. Rep. of Germany ....... 3808048

[51] Int. Cl.$^5$ .......................... C07K 3/18; C07K 3/28; C07K 15/06
[52] U.S. Cl. ...................... 530/381; 530/413; 530/412; 530/415
[58] Field of Search ................ 530/413, 415, 412, 381

[56] References Cited

U.S. PATENT DOCUMENTS 4,237,267 12/1980 Okuyama et al. ...................... 536/1
4,828,989 5/1989 Prior et al. ............................. 435/68

OTHER PUBLICATIONS

Abstract, Dialog File 72, Embase No: 87014291 of Grundman et al., 1986, Proc. Natl. Acad. Sci. U.S.A. 83(21): 8024-8028.

Biochimica et Biophysica Acta, "Affinity Chromatography of Human Plasma and Platelet Factor XIII on Organomercurial Agarose", J. McDonagh et al., vol. 446, pp. 345-357 (1976).

Biochemistry, "Calcium-Dependent Unmasking of Active Center Cysteine During Activation of Fibrin Stabilizing Factor", C. G. Curtis et al., vol. 13, No. 18, pp. 3774-3780 (1974).

Primary Examiner—Margaret Moskowitz
Assistant Examiner—Keith C. Furman
Attorney, Agent, or Firm—Finnegan, Henderson, Farabow, Garrett and Dunner

[57] ABSTRACT

The invention relates to a method for the purification of the a subunit of factor XIII by affinity chromatography, to a therapeutic composition containing the latter, and to the use of the therapeutic composition.

Factor XIII has hitherto been purified either by methods which are technically very elaborate or else by use of toxic affinity chromatography materials. The invention has the aim of providing an improved method for the purification of the a subunit of factor XIII.

Factor XIII is obtained according to the invention by a method in which the a subunit of factor XIII is reversibly bound to a matrix suitable for disulfide exchange reactions and is removed from the matrix by reaction with a reducing agent. The method according to the invention makes it possible to provide the biologically active a subunit of factor XIII in high purity.

14 Claims, No Drawings

METHOD FOR THE PURIFICATION OF FACTOR XIII BY AFFINITY CHROMATOGRAPHY

The invention relates to a method for the purification of the "a" subunit of factor XIII by affinity chromatography, to a therapeutic composition, and to the use of the therapeutic composition.

BACKGROUND OF THE INVENTION

The body has two systems, which are in equilibrium, in order to protect itself both from blood loss and from thromboses: the coagulation system and the fibrinolytic system. The interaction between these two systems ensures that there is initial production, for hemostasis, of insoluble fibrin polymers which are broken down again during wound healing by the lytic process of fibrinolysis.

The formation of stable thrombi as the final stage in the coagulation process is, moreover, the result of an intermeshed process which takes place like a cascade and during the progress of which each enzyme which has already been activated activates, by proteolysis, the following enzyme in the cascade and thereby amplifies the response of the body to the injury which has occurred. One of the last critical steps in this process is the polymerization of fibrin monomers. After the fibrin monomers have been formed they initially arrange themselves parallel alongside one another under the action of electrostatic forces. However, in this state they are connected only by hydrogen bonds and can be reliquefied by reagents which break hydrogen bonds, for example urea. Covalent bonding between the fibrin monomers then takes place in the presence of calcium ions by the formation of peptide linkages between the various monomers. The enzyme responsible for this network formation is activated factor XIII, called factor XIII a.

Factor XIII is a proenzyme of the blood coagulation system and can be detected both in plasma and in platelets. In plasma it occurs as a complex of "a" and "b" subunits which are not, however, covalently bonded together, whereas the form occurring in the platelets is composed only of "a" subunits. The two molecular forms of factor XIII have the same enzymatic function. After activation by thrombin and calcium, the factor XIII which has now been activated (factor XIIIa) catalyzes the formation of peptide-like linkages between particular lysine and glutamine residues in the fibrin, which results in covalent bonding of the fibrin monomers to give a network.

A genetically determined deficiency of factor XIII, or a factor XIII activation which is diminished by inhibitors, results in serious disturbances of blood coagulation. For this reason, various methods for the purification of factor XIII both from plasma and from platelets have been developed. These methods, some of which are very elaborate, are based on known protein-purification steps, for example fractional ethanol precipitation, ammonium sulfate and polyethylene glycol precipitations, as well as ion exchange chromatography or gel filtration. The authors Jan McDonagh et al. (Biochimica et Biophysica Acta, 446 (1976), 345-357) were the first to describe a method for the purification of factor XIII by affinity chromatography. They used for this purpose mercury benzoates coupled to agarose. The method provides for the reversible binding of the "a" subunit of plasma factor XIII to the mercury compound. Jan McDonagh et al. state that the "b" subunit, which itself contains no free thiol groups and thus cannot interact with the chromatography matrix, of the plasma factor remains bound to the a subunit by noncovalent forces until the latter is preactivated, by cleavage with thrombin, and is completely activated by subsequent treatment with calcium. A preparation of pure "a" subunits is thus possible by the method described by the said authors only after treatment with calcium and thrombin. Furthermore, the mercury compounds which they use are highly toxic; hence the described method cannot be used to prepare human therapeutics.

SUMMARY OF THE INVENTION

Hence the object of the present invention was to provide an improved method for the purification of the "a" subunit of factor XIII, in which the use of toxic compounds can be avoided.

This object is achieved according to the invention in a method of the abovementioned type by the "a" subunit of factor XIII being reversibly bound to a carrier matrix suitable for disulfide exchange reactions, and being removed from the carrier matrix by reaction with a reducing agent.

The reversible binding of the "a" subunit of factor XIII to carrier matrices suitable for disulfide exchange reactions has the advantage that it is possible to avoid the use of toxic chromatography materials. Furthermore, all the proteins contained in the factor XIII-containing solution can, by reason of a lower reactivity toward free mercapto groups or as a consequence of a behavior in the subsequent elution which differs from that of factor XIII, be separated from factor XIII using an agent which reduces the disulfide bonds. It is furthermore possible in the method according to the invention to remove the "b" subunits of plasma factor XIII from "a" subunits. It has been found, surprisingly, that, in contrast to the opinion expressed by McDonagh, the plasma factor XIII complex breaks down into "b" subunits and biologically active "a" subunits by incubation in calcium- or magnesium-containing solution in the absence of thrombin. Because the "b" subunits themselves do not have free mercapto groups, on the contrary all the SH groups provided by cysteines being in the form of disulfide bonds within the "b" subunits, they do not bind to the carrier matrix and can be removed by washing.

Factor XIII is preferably obtained from homogenates of materials with a high factor XIII concentration. These include, for example, placental tissue and blood platelets. The factor XIII isolated from these two materials is composed only of the "a" subunit.

Biologically active factor XIII can likewise be obtained from plasma. However, as already mentioned, plasma factor XIII is composed of a complex of two subunits which are not covalently bonded together, the "a" and the "b" subunit. The biologically active "a" subunit is obtained from this factor XIII complex according to the invention.

For the method according to the invention, factor XIII, irrespective of its origin, is made available in a solution for the purification by affinity chromatography. For this purpose, the appropriate biological material is prepared, for example, by removal by precipitation or centrifugation of higher molecular weight proteins from the blood or by homogenization and subsequent centrifugation of factor XIII-containing tissue.

The publication by C. G. Curtis et al. (Biochemistry 13, 1974, 3774–3780) discloses that a treatment of factor XIII with alkylating reagents in the absence of bivalent ions of group IIa of the periodic table has no effect on the biological activity of factor XIII. These authors were able to show that the active cysteine of factor XIIIa in the "a" subunit is normally in protected form. Only on simultaneous administration of calcium ions is this cysteine exposed by a change in conformation and is therefore likewise accessible to alkylation; the factor XIIIa which is thus completely S-alkylated is inactive even after cleavage by thrombin. Surprisingly, it has emerged that it is possible by treatment of the factor XIII-containing solution with alkylating agents in the absence of calcium or equivalent ions and subsequent purification by affinity chromatography to obtain a biologically active factor XIII preparation of higher purity.

Alkylating agents which are preferably used for this are iodoacetamide or iodoacetic acid. However, it is also possible according to the invention to use any other agent of similar alkylating capacity.

The particular alkylating agents for the alkylation by procedures known in the state of the art should be added at a concentration of approximately 5–100 mmol/l. A preferred embodiment provides for the treatment with iodoacetic acid at a concentration of 5–50 mmol/l.

According to the invention, the alkylation is carried out in the absence of $Ca^{2+}$ or ions having a similar action. If this is not the case, owing to changes in the conformation of the a subunit the active center also becomes accessible to alkylation and is thus blocked. It is therefore sensible to use buffers free of $Ca^{2+}$ and $Mg^{2+}$.

In a preferred embodiment, the alkylation is carried out in the presence of added chelating agents. Particularly preferably used for this purpose is ethylenediaminetetraacetic acid (EDTA) in a concentration between 0.001 and 0.1 mol/l.

According to the invention, the alkylation of the factor XIII-containing solution is carried out at a pH at which factor XIII undergoes no major changes in conformation. A preferred pH is therefore one in the neighborhood of the physiological pH, i.e. the alkylation is carried out at a pH between 6.5 and 8.5. In order to prevent the active center of the "a" subunit being exposed by $Ca^{2+}$-induced changes in the tertiary structure of the molecule, it is preferable to add to the reaction mixture between 0.001 and 0.04 mol/l EDTA. The alkylation is then carried out, for example, with 0.005–0.25 mol/l iodoacetic acid. However, higher or lower concentrations of the iodoacetic acid are also conceivable. The reaction is normally carried out for between one and 360 min. However, the reaction should not take more than 5 min to obtain complete alkylation of exposed mercapto groups. No limits are placed on the reaction time, but adequate carboxymethylation of exposed mercapto groups can be expected after not more than 60 min.

After the alkylation has been carried out, the alkylating substance is removed again from the solution. This can be carried out by methods known to those skilled in the art, for example by gel filtration, salt precipitation and/or dialysis. Any other method is equally applicable for this purpose provided the alkylating substance is quantitatively removed from the solution thereby.

On isolation of the active "a" subunit from plasma factor XIII, the latter must be separated from the non-covalently associated "b" subunit. This is preferably carried out by incubation of the plasma factor XIII, which has already been alkylated where appropriate, with calcium or magnesium ions in a concentration of 0.05–0.6 mol/l, particularly preferably 0.05–0.2 mol/l. After incubation in the presence of calcium or magnesium for 5 minutes to two hours the "a" and "b" subunits are in a dissociated state. In the isolation of the "a" subunit from plasma factor XIII this dissociation of the subunits is a necessary precondition for carrying out the adsorption, which is described hereinafter, on material suitable for disulfide exchange reactions.

The factor XIII-containing solution, which has either not been pretreated or else been previously treated with an alkylating substance, is subsequently brought into contact with the carrier matrix which is suitable for disulfide exchange reactions and which contains free mercapto groups. An example of a preferred material suitable for disulfide exchange reactions is thiol-Sepharose 4B. The reaction can take place both in the so-called batch method and on preparative columns.

According to the invention, the factor XIII-containing solution is brought into contact with the matrix in the presence of calcium or magnesium ions, preferably in a concentration of 0.01–0.2 mol/l. The adsorption should take place at virtually physiological pH, preferably at a pH between 6.5 and 8.5.

The mercapto groups of the carrier matrix are, according to the invention, previously activated in a manner known per se by reaction with di-2-pyridyl disulfide, 2,2'-dithiobis(pyridine N-oxide), 5,5'-dithiobis(2-nitrobenzoic acid), derivatives of these compounds or derivatives of azodicarboxylic acid and thus prepared for the formation of disulfide bonds with the sample which is applied later.

After the factor XIII has been bound to the matrix which contains mercapto groups, this matrix is washed with a solution which contains calcium or magnesium in a concentration of 0.01–0.2 mol/l. All the other constituents in the factor XIII-containing solution which are unable to interact with the matrix, whether because they themselves contain no cysteines or else because their mercapto groups have previously been alkylated, are eluted quantitatively, and in the case of factor XIII from plasma also the "b" subunits which have been separated from the a subunit by treatment with calcium or magnesium.

In a following step in the method, the "a" subunit of factor XIII is eluted from the matrix. It is possible to use as eluent for this every agent which is suitable for disulfide exchange reactions and which replaces the factor XIII "a" subunit coupled to the matrix and, at the same time, reduces the disulfide bond between the matrix and the "a" subunit. A preferred embodiment provides for elution with 0.005–0.05 mol/l of a reducing agent, preferably dithiothreitol, mercaptoethanol, ethanedithiol, glutathione or cysteine, in the presence of 0.01–0.2 mol/l $Ca^{2+}$ or $Mg^{2+}$. A particularly preferred embodiment, which results in an increase in the yield of active "a" subunit, provides for the addition of 0.1–0.7 g of sucrose/ml of eluent.

This method can be applied not only to factor XIII isolated from natural sources but equally to factor XIII produced by genetic manipulation in bacteria, yeasts or cell cultures. Furthermore, it can be applied to every protein having factor XIII activity provided the cysteine of the active center continues to be subject to the effects of a change in conformation by addition of calcium ions or ions having a similar action.

The method according to the invention results in a factor XIII preparation whose activity is almost completely retained during the purification.

The factor XIII obtained by the method according to the invention can be used for therapeutic compositions. Preferred compositions in this connection are factor XIII-containing solutions which, besides factor XIII, contain physiologically tolerated constituents, for example sodium chloride, albumin, glucose or sucrose, and are suitable for infusions.

A therapeutic of this type can be used, in particular, for the therapy of factor XIII-deficiency disorders. Another preferred use of the factor XIII obtained according to the invention is, for example, admixture in stored blood products or erythrocyte concentrates in order to retain the clotting ability of the blood given after large blood losses.

The method according to the invention for the purification of factor XIII is explained by the examples which follow.

Example 1

Activation of THIOL-SEPHAROSE 4B ® with di-2-pyridyl disulfide, Ellmann's reagent or 2,2'-dithiobis(pyridine N-oxide)

50 ml of THIOL-SEPHAROSE 4B, bead-formed agarose gels produced by Pharmacia, Sweden, were initially treated at room temperature (RT) for 30 min with buffer A (0.05 mol/l tris/HCl pH 7.5, 0.15 mol/l NaCl) to which 0.03 mol/l mercaptoethanol had been added. The resin material was subsequently washed with buffer A and reacted with this buffer to which 1.5 mmol/l di-2-pyridyl disulfide had also been added. After activation and protection of the mercapto groups on the resin matrix was complete, it was washed with buffer A, and the resin matrix was used for the disulfide exchange reaction.

It is also possible to use for the activation in place of di-2-pyridyl disulfide, for example, in the same molarity 5,5'-dithiobis(2-nitrobenzoic acid) (Ellmann's reagent) or 2,2'-dithiobis(pyridine N-oxide).

Example 2

Reaction of a factor XIII-containing solution with activated THIOL-SEPHAROSE 4B ®

50 ml of a factor XIII-containing solution which contained 700 U of factor XIII (1 U of factor XIII corresponds to the content of factor XIII in 1 ml of citrated normal plasma) were saturated with 40% (w/v) ammonium sulfate.

The ammonium sulfate residue was dialyzed against buffer A (Example 1) at 4° C. overnight and subsequently 30 mmol/l $CaCl_2$ were added. The activated thiol resin, which had been activated, for example, as described in Example 1, was equilibrated with buffer A to which 30 mmol/l $CaCl_2$ had been added. The calcium-containing dialysate was loaded onto the prepared affinity matrix, the resin material was subsequently washed with buffer A, 30 mmol/l $CaCl_2$, and factor XIII was eluted with buffer A to which 15 mmol/l dithiothreitol and 30 mmol/l $CaCl_2$ had been added. The eluate contained 500 U of factor XIII.

Example 3

The activation of the THIOL-SEPHAROSE 4B and its reaction with a factor XIII-containing solution were carried out as described in Examples 1 and 2 but 0.5 g of sucrose/ml of solution was also added to the washing and eluting buffers. The eluate contained 600 U of factor XIII.

Example 4

Reaction of a plasma factor XIII-containing solution with activated THIOL-SEPHAROSE 4B ®

50 ml of a plasma factor XIII-containing solution which contained 1,000 units of factor XIII but no thrombin were dialyzed against buffer A (Example 1) at 4° C. overnight and subsequently 0.3 mol/l $CaCl_2$ and 0.1 g of sucrose/ml were added. After an incubation time of 60 min at 4° C., the solution was applied to a thiol resin which had been activated, for example as described in Example 1, and had been equilibrated with buffer B, composed of 0.05 mol/l tris/HCl pH 7.5, 0.15 mol/l NaCl, 0.1 mol/l $CaCl_2$ and 0.1 g of sucrose/ml. The resin material was subsequently washed with buffer B and eluted with buffer B to which 20 mmol/l L-cysteine had been added. The eluate contained 820 U of factor XIII and was free of "b" subunits.

Example 5

Alkylation of a F XIII-containing solution and subsequent reaction with activated THIOL-SEPHAROSE 4B ®

50 ml of a factor XIII-containing solution which contained 700 U of factor XIII were dialyzed against buffer A to which 5 mmol/l EDTA had been added, and were incubated with 10 mmol/l iodoacetic acid at RT for 1 h. The solution was saturated with 40% (w/v) ammonium sulfate, and the precipitate was further processed as described in Example 2.

The recovery in the eluate was 450 U of factor XIII without added sucrose, and was 580 U of factor XIII with added sucrose in the washing and eluting buffers. The purity of factor XIII eluted from the affinity resin after alkylation was distinctly greater than that of a non-alkylated factor XIII material.

The biological activity of factor XIII in a solution was determined using a fibrin crosslinking test of Behringwerke AG. For this purpose, the samples were diluted 1:5, 1:10, 1:20, 1:40 etc. in serial dilutions with diethylbarbiturate/acetate buffer, pH 7.6. Subsequently 0.1 ml of Ca/thrombin/kaolin solution was added to 50 $\mu$l of each sample dilution, and the mixtures were incubated at 37° C. for 10 min. Immediately thereafter 1 ml of 5% monochloroacetic acid solution was added to each, incubation was continued for 2 min and, after vigorous shaking, the kaolin turbidity of the solution was determined.

We claim:

1. A method for the purification of the "a" subunit of factor XIII by affinity chromatography, which comprises:
    alkylating a solution containing the "a" subunit of factor XIII in the absence of $Ca^{2+}$ and $Mg^{2+}$;
    reversibly binding the "a" subunit of factor XIII to a carrier matrix suitable for disulfide exchange reactions in the presence of at least one of $Ca^{2+}$ and $Mg^{2+}$; and removing the "a" subunit of factor XIII from the carrier matrix by reaction with a reducing agent.

2. The method as claimed in claim 1, wherein the a subunit of factor XIII is obtained from placental homogenate or platelet homogenate or plasma.

3. The method as claimed in claim 1, wherein the a subunit of factor XIII is obtained from plasma.

4. The method as claimed in claim 1, wherein the alkylating agent is iodoacetamide or iodoacetic acid.

5. The method as claimed in claim 1, wherein the alkylation takes place in the presence of chelating substances in a concentration of 0.001–0.1 mol/l.

6. The method as claimed in claim 1, wherein a factor XIII-containing solution is brought into contact with a carrier matrix which contains mercapto groups.

7. The method as claimed in claim 1, wherein the binding to the carrier matrix takes place in the presence of at least one of $Ca^{2+}$ and $Mg^{2+}$ in a concentration of 0.01–0.2 mol/l and at pH 6.5–8.5.

8. The method as claimed in claim 1, wherein the carrier matrix has previously been activated by reaction with at least one of the group selected from di-2-pyridyl disulfide, 2,2'-dithiobis(pyridine N-oxide), 5,5'-dithiobis(2-nitrobenzoic acid), which derivatives of these compounds which activate thiol groups and derivatives of azodicarboxylic acid which activate thiol groups.

9. The method as claimed in claim 1, wherein material bound to the carrier matrix is eluted with 0.01–0.2 mol/l $Ca^{2+}$ or $Mg^{2+}$ and 0.005–0.05 mol/l of a reducing agent selected from at least one of the group consisting of dithiothreitol, mercaptoethanol, ethanedithiol, glutathione and cysteine.

10. The method as claimed in claim 1, wherein the source for said "a" subunit of factor XIII is selected from the group consisting of natural protein, a factor XIII which has been produced by genetic manipulation or the "a" subunit thereof, and naturally or artificially generated protein having factor XIII activity and which contains a free thiol group which does not become alkylated in the absence of $Ca^{2+}$ and $Mg^{2+}$.

11. The method as claimed in claim 1, wherein the alkylation takes place in the presence of ethylenediaminetetraacetic acid in a concentration of 0.001–0.1 mol/l.

12. The method as claimed in claim 1, wherein the aklylation takes place in the presence of ethylenediaminetetraacetic acid in a concentration of 0.002–0.02 mol/l.

13. The method as claimed in claim 9, wherein material bound to the carrier matrix is eluted with 0.1–0.7 g of sucrose/ml.

14. A method for the purification of the "a" subunit of factor XIII by affinity chromatography, which comprises:

liberating the "a" subunit of factor XIII from plasma factor XIII complex by incubation with at least one of $Ca^{2+}$ and $Mg^{2+}$ in a concentration of 0.05–0.6 mol/l in the absence of thrombin;

reversibly binding the "a" subunit of factor XIII to a carrier matrix suitable for disulfide exchange reactions; and removing the "a" subunit of factor XIII from the carrier matrix by reaction with a reducing agent.

* * * * *

UNITED STATES PATENT AND TRADEMARK OFFICE
CERTIFICATE OF CORRECTION

PATENT NO. : 5,047,506

DATED : September 10, 1991

INVENTOR(S) : Hartmut Lobermann et al.

It is certified that error appears in the above-identified patent and that said Letters Patent is hereby corrected as shown below:

Claim 8, column 7, line 24, before "derivatives" delete "which".

Claim 12, column 8, line 14, change "aklylation" to --alkylation--.

Signed and Sealed this

Twenty-third Day of March, 1993

Attest:

STEPHEN G. KUNIN

*Attesting Officer*   *Acting Commissioner of Patents and Trademarks*